United States Patent [19]
Bremecker et al.

[11] Patent Number: 4,891,226
[45] Date of Patent: Jan. 2, 1990

[54] PHARMACEUTICAL WHICH CAN BE ADMINISTERED NASALLY, A PROCESS FOR ITS PREPARATION, AND ITS USE

[75] Inventors: Klaus-Dieter Bremecker; Klaus-Dieter Hungerer; Hansjörg Ronneberger, all of Marburg, Fed. Rep. of Germany

[73] Assignee: Behringwerke Aktiengesellschaft, Marburg, Fed. Rep. of Germany

[21] Appl. No.: 284,812

[22] Filed: Dec. 14, 1988

Related U.S. Application Data

[63] Continuation of Ser. No. 5,640, Jan. 21, 1987, abandoned.

[30] Foreign Application Priority Data

Jan. 23, 1986 [DE] Fed. Rep. of Germany ....... 3601923

[51] Int. Cl.$^4$ ................ A61K 9/00; A61K 39/02; A61K 39/12; A61K 37/24
[52] U.S. Cl. .................................. 424/434; 424/85.1; 424/88; 424/485
[58] Field of Search ................. 424/85-89, 424/434, 435, 484-488

[56] References Cited

U.S. PATENT DOCUMENTS

| 4,226,848 | 10/1980 | Nagai et al. | 424/434 |
| 4,250,163 | 2/1981 | Nagai et al. | 424/434 |
| 4,292,299 | 9/1981 | Suzuki et al. | 424/434 X |
| 4,394,390 | 7/1983 | Hussain et al. | 424/434 X |
| 4,476,116 | 10/1984 | Anik . | |

FOREIGN PATENT DOCUMENTS

| 0115627 | 12/1983 | European Pat. Off. . | |
| 0122036 | 3/1984 | European Pat. Off. . | |
| 0193372 | 2/1986 | European Pat. Off. . | |
| 7521022 | 1/1976 | France . | |
| 0118413 | 9/1980 | Japan | 424/434 |
| 0118414 | 9/1980 | Japan | 424/434 |

Primary Examiner—Nancy A. B. Swisher
Attorney, Agent, or Firm—Finnegan, Henderson, Farabow, Garrett and Dunner

[57] ABSTRACT

A pharmaceutical which is for nasal administration and contains a high molecular weight active compound and a gel-forming agent and, where appropriate, auxiliaries is described. High molecular weight active compounds of this type are, in particular, immunogens or other pharmacologically effective substances. In addition, a process for the preparation of a pharmaceutical of this type and its use are described.

10 Claims, No Drawings

PHARMACEUTICAL WHICH CAN BE ADMINISTERED NASALLY, A PROCESS FOR ITS PREPARATION, AND ITS USE

This application is a continuation of application Ser. No. 005,640 filed Jan. 21, 1987, now abandoned.

The present invention relates to pharmaceuticals which can be administered nasally, by incorporation of immunogenic, antigenic or other high molecular weight active compounds in gels, to a process for the preparation of pharmaceuticals of this type, and to their use.

Effective vaccines are among the agents which are best and most economic for preventing infectious diseases. Those which have proved particularly useful are bacterial vaccines such as those against tetanus, diphtheria and pertussis, or viral vaccines such as those against polio, smallpox and measles. Apart from the great efficacy of many products, however, account always has to be taken of the possibility of side effects. The causes of such side effects are often directly connected with the active component (for example lipopolysaccharides of Gram-negative bacteria), the adjuvant (for example oil-containing preparations) or, possibly, the mode of administration. Most of the vaccines developed in the last 80 years have to be administered parenterally. This mode of administration has the great advantage that an exactly defined dose can be administered reproducibly at any time. Certain side effects might be a certain disadvantage, such as hyperergic or neuroparalytic reactions which are directly connected with the parenteral administration.

For this reason, modes of administration other than parenteral have been examined. Thus, it is nowadays possible to build up protection against typhoid fever after oral administration of the vaccine. Oral, sublingual administration of tetanus toxoid has also been described.

However, the nasal cavity has proved to be particularly interesting for the topical application of vaccines and other pharmaceutically effective products (U.S. Pat. No. 4,476,116). The known products are nasal drops or nasal sprays. These pharmaceutical forms have the disadvantage that accurate dosage of the effective amount of substance is difficult, because at every administration an unknown amount of the active substance passes via the nasopharynx to the digestive tract and, once there, is normally unable to exert the desired effect.

It has been found, surprisingly, that vaccines and other high molecular weight pharmacologically effective products can be accurately dosed on nasal administration if the fluidity of the aqueous preparation is specifically limited by gel-forming agents.

Hence the invention relates to a pharmaceutical for nasal administration, which contains a high molecular weight active compound and a gel-forming agent and, where appropriate, auxiliaries.

A high molecular weight active compound of this type can be an immunogen, preferably a bacterial or viral immunogen, or a pharmacologically effective substance, preferably a hormone, especially a peptide hormone.

The gel-forming agent is composed of an organic or inorganic hydrogel-forming agent, preferably hydroxyethylcellulose, for example Tylose ®H 4000 (Hoechst AG, Frankfurt), or colloidal disperse silica, for example Aerosil ® (Degussa, Frankfurt), in a concentration of 1-15, preferably 2-8, g/100 g.

The gel is stabilized by additives, preferably Na dodecyl sulfate or Na lauryl sulfate, for example Texapon ® L 100 (Henkel, Düsseldorf) or Na cetyl/stearyl sulfate such as, for example, Lanette ® E (Henkel, Düsseldorf), in a concentration of 0.05-15, preferably 0.1-8, g/100 g.

The solvent or swelling agent which is preferably used is water. It is possible to add to the gel auxiliaries, for example humectants such as propylene glycol, glycerol, sorbitol or polyethylene glycol (PEG). For preservation it is possible to use non-ionic or ionic preservatives, preferably propylene glycol, Na timerfonate, sorbic acid, or benzoic acid derivatives. Preparation can be carried out with the machines and equipment customary for the preparation of ointments and with appropriate precautions.

In order to avoid deterioration of the active compound which is to be incorporated, initially the gel base is prepared by a procedure customary in pharmaceutical technology. The active compound is then incorporated, in dissolved, suspended or dry form and in suitable concentration, into the prepared base.

It is possible with a formulation of this type to deliver a sufficiently accurate dose of the active substance onto the nasal mucosa, which makes it possible to control the desired reaction within the scope of biological reproducibility. It can be applied in the manner of a nasal ointment.

The preparation of a formulation of this type corresponds to the usual production of ointments.

Both the base containing no active compound and the finished preparation are tolerated by the mucosa without detectable irritation even after several applications. It has been shown, using the example of tetanus and diphtheria toxoid as active compound, that, compared with conventional nasal preparations (solution, spray or ointment), the bioavailability is optimized and the variation in the titer is minimized.

The vehicle system which has been described was suitable for the incorporation of low molecular weight active compounds as well as of macromolecules, in particular of toxoids such as those of tetanus, Staph. aureus or diphtheria, or of bacterial extracts such as those of Pseudomonas, or of hormones, especially of peptide hormones such as insulin, or of anticoagulants such as Liquemin ®, or of immunoglobulins containing polyclonal or monoclonal antibodies.

The pharmaceuticals according to the invention can be used for the prophylaxis or therapy of diseases.

These pharmaceuticals can be administered to humans or animals.

The preparation of some formulations is described by way of example hereinafter.

| Example 1 | |
|---|---|
| Aerosil ® 200 | 0.5 g |
| Lanette ® E | 0.5 g |
| Tetanus toxoid (TT; 2000 LF*/ml) | 2.5 ml |
| Diphtheria toxoid (DT; 2000 LF/ml) | 2.5 ml |
| Water ad | 10.0 g |

Aerosil ® was suspended in the aqueous solution of Lanette ® E with the formation of a gel. The two solutions containing active compounds were incorporated. 0.2 g of the preparation corresponded to 100 LF TT and DT.

(*) LF=Limes flocculationis (WHO Requirements, Technical Report Series (1964), 293)

Example 2

| | |
|---|---|
| Tylose ® H 4000 (6%) | 4.9 g |
| Texapon ® L 100 | 0.1 g |
| TT (2000 LF/ml) | 2.5 ml |
| DT (2000 LF/ml) | 2.5 ml |

Texapon ® was dissolved in Tylose mucilage, and the TT and DT solutions were incorporated.

Example 3

| | |
|---|---|
| Lanette ® N | 0.5 g |
| Propylene glycol | 1.0 g |
| Karion ® F (sorbitol, liquid; Merck, Darmstadt) | 2.0 g |
| TT (2000 LF/ml) | 2.5 ml |
| DT (2000 LF/ml) | 2.5 ml |
| water ad | 10.0 g |

Lanette ® N, propylene glycol, Karion ® F and water were homogenized while heating. The toxoids were incorporated in the resulting base.

The preparations in the examples which follow were prepared as described in Example 1.

Example 4

| | |
|---|---|
| Aerosil ® 200 | 0.6 g |
| Texapon ® L100 (10% aqueous solution) | 5.4 g |
| Staph. aureus alpha-toxin-toxoid (600 BU) | 1.0 ml |

Example 5

| | |
|---|---|
| Aerosil ® 200 | 0.24 g |
| Lanette ® E (10% aqueous solution) | 5.4 g |
| Pseudomonas extract prepared as stated in Behring Institute Mitteilungen, No. 76, 113–120 (1984); "Vaccine production" | 0.2 g |
| Water ad | 4.8 g |

Example 6

| | |
|---|---|
| Aerosil ® 200 | 0.4 g |
| Lanette ® E (10% aqueous solution) | 3.6 g |
| Insulin CR (Hoechst AG) | 2 g |
| Water | 2 g |

Example 7

| | |
|---|---|
| Aerosil ® 200 | 0.5 g |
| Lanette ® E (10% aqueous solution) | 4.5 g |
| Liquemin ® 2500 (sodium heparinate; Hoffmann-La Roche) | 4 ml |
| Water ad | 10 g |

We claim:

1. A pharmaceutical gel composition for vaccination through nasal administration, which contains a high molecular weight active compound, in a concentration effective to vaccinate, in a gel-forming agent and, where appropriate, auxiliaries.

2. A pharmaceutical gel composition as claimed in claim 1, wherein the active compound is an immunogen or another pharmacologically effective substance.

3. A method for the prevention or treatment of diseases, comprising the administration to a patient of an effective amount of the pharmaceutical gel composition of claim 2.

4. A pharmaceutical gel composition as claimed in claim 1, wherein the gel-forming agent is an organic or inorganic hydrogel-forming agent in a concentration of 1–15 g/100 g.

5. A method for the prevention or treatment of diseases, comprising the administration to a patient of an effective amount of the pharmaceutical gel composition of claim 4.

6. A pharmaceutical gel composition as claimed in claim 1, wherein the gel-forming agent is hydroxyethylcellulose or colloidal disperse silica in a concentration of 1–15 g/100 g.

7. A method for the prevention or treatment of diseases, comprising the administration to a patient of an effective amount of the pharmaceutical gel composition of claim 6.

8. A pharmaceutical gel composition as claimed in claim 1, which contains a humectant and/or preservative.

9. A process for the preparation of a pharmaceutical gel composition as claimed in claim 1, which comprises preparing the gel base and incorporating the active compound in dissolved, suspended or dry form and in effective concentration.

10. A method for the prevention or treatment of diseases, comprising the administration to a patient of an effective amount of the pharmaceutical gel composition of claim 1.

* * * * *